US011701340B2

(12) United States Patent
Dhanarajan et al.

(10) Patent No.: US 11,701,340 B2
(45) Date of Patent: Jul. 18, 2023

(54) LIQUID PHARMACEUTICAL COMPOSITIONS

(71) Applicant: Vici Health Sciences LLC, Elkridge, MD (US)

(72) Inventors: Anish Dhanarajan, Catonsville, MD (US); Francesca Minale, Catonsville, MD (US)

(73) Assignee: VICI HEALTH SCIENCES., LLC, Elkridge, MD (US)

( * ) Notice: Subject to any disclaimer, the term of this patent is extended or adjusted under 35 U.S.C. 154(b) by 0 days.

(21) Appl. No.: 16/851,242

(22) Filed: Apr. 17, 2020

(65) Prior Publication Data

US 2020/0330431 A1      Oct. 22, 2020

Related U.S. Application Data

(60) Provisional application No. 62/835,123, filed on Apr. 17, 2019.

(51) Int. Cl.
| | |
|---|---|
| *A61K 31/135* | (2006.01) |
| *A61K 9/08* | (2006.01) |
| *A61K 47/10* | (2017.01) |
| *A61K 47/12* | (2006.01) |
| *A61P 25/16* | (2006.01) |
| *A61K 31/404* | (2006.01) |

(52) U.S. Cl.
CPC .............. *A61K 31/404* (2013.01); *A61K 9/08* (2013.01); *A61K 31/135* (2013.01); *A61K 47/10* (2013.01); *A61K 47/12* (2013.01)

(58) Field of Classification Search
CPC ........ A61K 31/135; A61K 9/08; A61K 47/10; A61K 47/12; A61P 25/16

USPC ........................................... 514/647; 564/308
See application file for complete search history.

(56) References Cited

U.S. PATENT DOCUMENTS

| | | | |
|---|---|---|---|
| 5,744,500 A | * | 4/1998 | Youdim ................ C07C 211/30 514/647 |
| 5,807,570 A | | 9/1998 | Chen et al. |
| 2010/0010095 A1 | * | 1/2010 | Frenkel ................... A61P 25/16 514/647 |
| 2014/0275202 A1 | | 9/2014 | Schmitz et al. |
| 2016/0022572 A1 | | 1/2016 | Youdim et al. |

FOREIGN PATENT DOCUMENTS

| | | |
|---|---|---|
| EP | 2526924 A1 | 11/2012 |
| WO | 2015136543 A1 | 9/2015 |

OTHER PUBLICATIONS

Jiang et al., Preparation and evaluation of injectable Rasagiline mesylate dual-controlled drug delivery system for the treatment of Parkinson's disease, Drug Delivery, 2018, 25(1), 143-152.
International Search Report and Written Opinion of corresponding PCT Application No. PCT/US2020/028633 dated Jul. 21, 2020.

\* cited by examiner

*Primary Examiner* — Irina Neagu
(74) *Attorney, Agent, or Firm* — Wood, Phillips, Katz, Clark & Mortimer

(57) ABSTRACT

The present invention is directed to liquid pharmaceutical compositions comprising an active ingredient selected from the group consisting of rasagiline, ropinirole and a pharmaceutically acceptable salt thereof and a liquid vehicle. The present invention is further directed to methods of treating Parkinson's disease or one or more symptoms of Parkinson's disease comprising administering a liquid pharmaceutical composition of the present invention to a subject in need thereof.

3 Claims, No Drawings

LIQUID PHARMACEUTICAL COMPOSITIONS

FIELD OF THE INVENTION

The present invention is directed to liquid pharmaceutical compositions comprising an active ingredient selected from the group consisting of rasagiline, ropinirole and pharmaceutically acceptable salts thereof and a liquid vehicle. The present invention is further directed to methods of treating Parkinson's disease or one or more symptoms of Parkinson's disease comprising administering a liquid pharmaceutical composition of the present invention to a subject in need thereof.

BACKGROUND OF THE INVENTION

Parkinson's disease is a chronic and degenerative nervous system disorder that causes loss of control of body function and movement. At least one million people in the United States, and more than five million people worldwide, have been diagnosed with Parkinson's disease. This includes about 1 in 100 people over the age of 60.

Parkinson's disease has a myriad of symptoms and complications. Symptoms of Parkinson's disease include tremors, bradykinesia, rigid muscles, impaired posture and balance, loss of automatic movements, speech changes and writing changes. Complications of Parkinson's disease include difficulty thinking, depression, difficulty in swallowing, chewing and eating, sleep disorders, bladder issues and constipation.

Several medications have been developed for the treatment of Parkinson's disease and its symptoms. These medications include levodopa, carbidopa, safinamide, ropinirole, pramipexole, bromocriptine, rotigotine, amantadine, trihexyphenidyl, benztropine, selegiline, rasagiline, tolcapone and entacapone. The majority of these medications, if not all, are available only in a solid tablet form.

Rasagiline, is a potent, selective, irreversible monoamine oxidase-type B (MAO-B) inhibitor for the treatment of Parkinson's disease. Rasagiline is currently only available in tablet form as a mesylate salt in Azilect® (Azilect is a registered trademark of and available from Teva Pharmaceutical Industries Ltd.). Azilect® is available in both a 0.5 and 1.0 milligram oral tablet.

Ropinirole, is a non-ergoline dopamine agonist for the treatment of Parkinson's disease. Ropinirole is currently only available in tablet form as a hydrochloride salt in Requip® and Requip XL® (Requip and Requip XL are registered trademarks of and available from Glaxo Group Limited Corporation). Requip® is available in a 0.25, 0.5, 3.0, 4.0 and 5.0 milligram oral tablet. Requip® XL is an extended release formulation available in a 2.0, 4.0, 6.0, 8.0 and 12.0 milligram oral tablet.

Dysphagia, or trouble swallowing, occurs in 91 to 94% of stage 2 and stage 3 Parkinson's disease patients. Nilsson H et al., Quantitative Assessment of Oral and Pharyngeal Function in Parkinson's Disease." *Dysphagia* 11: 144-150, 1996. Because of the dysphagia in Parkinson's disease patients administering solid oral medication is problematic. Healthcare providers report that administering Parkinson's disease medications in tablet form is difficult and uncomfortable for both the provider and the patient and can lead to compliance issues.

A common method for administering solid dosage forms to patients with dysphagia is to crush the solid dosage form and suspend the resulting powder in water. However, this method is highly problematic as many active ingredients are light and or water sensitive and thus degrade upon crushing and or suspension in water. Bowman C. Administration of drugs to patients with swallowing difficulties. *Journal of the Malta College of Pharmacy Practice* 12: 42-45, 2007. Further, many patients with dysphagia are fed through feeding tubes. These crushed tablets in water are the most common feeding tube obstruction. Bemt P, et al. Quality Improvement of Oral Medication Administration in Patients with Enteral Feeding Tubes. *Quality and Safety in Health Care* 2006:15: 44-47.

Thus, there exists a need in the art, for dosage forms of medications to treat Parkinson's disease that are easy to administer. Specifically, there is a need in the art for stable liquid oral compositions.

SUMMARY OF THE INVENTION

The present invention is directed to liquid pharmaceutical compositions comprising an active ingredient selected from the group consisting of rasagiline, ropinirole and a pharmaceutically acceptable salt thereof and a liquid vehicle comprising one or more carriers and one or more buffers.

The present invention is further directed to methods of treating Parkinson's disease or one or more symptoms of Parkinson's disease comprising administering a liquid pharmaceutical composition of the present invention to a subject in need thereof.

DETAILED DESCRIPTION OF THE INVENTION

The Applicant has discovered liquid compositions of rasagiline or ropinirole that are surprisingly stable. The stability of these liquid compositions of the present invention is unexpected in light of the prior art, which is devoid of stable liquid compositions of rasagiline or ropinirole.

In one embodiment, the present invention is directed to liquid pharmaceutical compositions comprising an active ingredient selected from the group consisting of rasagiline, ropinirole and a pharmaceutically acceptable salt thereof and a liquid vehicle comprising one or more carriers and one or more buffers.

In a preferred embodiment, the rasagiline is rasagiline mesylate.

In another preferred embodiment, the ropinirole is ropinirole hydrochloride.

In another preferred embodiment, the rasagiline or pharmaceutically acceptable salt thereof is present in compositions of the present invention at a concentration from about 0.001% to about 0.1% w/v, preferably from about 0.01% to about 0.05% w/v, more preferably from about 0.02% to about 0.035% w/v and most preferably at about 0.03% w/v.

In another preferred embodiment, the ropinirole or pharmaceutically acceptable salt thereof is present in compositions of the present invention at a concentration from about 0.001% to about 0.1% w/v, preferably from about 0.01% to about 0.05% w/v, more preferably from about 0.01% to about 0.03% w/v and most preferably at about 0.02% w/v.

In another preferred embodiment, the one or more carriers are selected from the group consisting of water, propylene glycol and glycerin, preferably a mixture of water and glycerin.

In another preferred embodiment, the one or more carriers are present in compositions of the present invention at a concentration from about 70% to about 120% w/v, more preferably from about 90% to about 115% w/v, even more preferably from about 95% to about 113% w/v and most preferably at about 112.644% w/v or about 100.94% w/v or about 101.93% w/v.

In a more preferred embodiment, water is present in compositions of the present invention at a concentration from about 10% to about 99.999% w/v, more preferably from about 10% to about 90% w/v, even more preferably from about 20% to about 70% w/v, yet even more preferably from about 40% to about 60% w/v or from about 50% to about 70% w/v and most preferably at about 55% w/v or about 56% w/v.

In another more preferred embodiment, glycerin is present in compositions of the present invention at a concentration from about 10% to about 99.999% w/v, more preferably from about 10% to about 90% w/v, even more preferably from about 40% to about 80% w/v, yet even more preferably from about 50% to about 70% w/v and most preferably at about 60% w/v.

In another more preferred embodiment, propylene glycol is present in compositions of the present invention at a concentration from about 10% to about 99.999% w/v, more preferably from about 10% to about 90% w/v, even more preferably from about 20% to about 60% w/v, yet even more preferably from about 30% to about 50% w/v and most preferably at about 40% w/v.

In a yet more preferred embodiment the one or more carriers are selected from: a mixture of from about 10% to about 90% w/v water and from about 10% to about 90% w/v glycerin; a mixture of from about 10% to about 90% w/v water and from about 10% to about 90% w/v propylene glycol; a mixture of from about 40% to about 60% w/v water and from about 50% to about 70% w/v glycerin; and a mixture of from about 50% to about 70% w/v water and from about 30% to about 50% w/v propylene glycol.

In another preferred embodiment, the one or more buffers are selected from the group consisting of acetate buffers, carbonate buffers, citrate buffers including citric acid and a citrate salt, phosphate buffers and borate buffers. In a preferred embodiment, the one or more buffers is a mixture of citric acid and a citrate salt.

Citrate salts include, but are not limited to, salts that pair a cation with the up to three carboxylate ions that can form from deprotonating the three carboxylic acid groups of citric acid. For example, a salt of sodium citrate may be formed by replacing one, two, or three of the carboxylic acid protons with sodium ions (i.e., monosodium citrate, disodium citrate, and trisodium citrate). The citrate salts may be added to compositions of the present invention as part of an aqueous solution, or as a solid. When added as solid, the citrate compound may be anhydrous, or more typically a hydrate that incorporates one or more water ("$H_2O$") group into the crystal structure of the compound. For example, solid sodium citrate may incorporate one or more water groups into the crystal structure, such as sodium citrate monohydrate (i.e., $1H_2O$), sodium citrate dihydrate (i.e., $0.2H_2O$), sodium citrate trihydrate (i.e., $3H_2O$), sodium citrate tetrahydrate (i.e., $0.4H_2O$), sodium citrate pentahydrate (i.e., $5H_2O$), sodium citrate hexahydrate (i.e., $6H_2O$), etc. Citrate salts may also include the hydrates and/or anhydrates of salts beyond sodium, such as other alkali metal or alkaline metal cations, ammonia, organic primary, secondary, or tertiary amines including, but not limited to; lithium, potassium, calcium, magnesium and aluminum cations and the like; nontoxic quaternary ammonia and amine cations including ammonium, tetramethylammonium, tetraethylammonium, methylammonium, dimethylammonium, trimethylammonium, triethylammonium, diethylammonium, and ethylammonium and the like; and organic amines including ethylenediamine, ethanolamine, diethanolamine, piperidine, piperazine and the like. In a preferred embodiment, the citrate salt is a sodium citrate. In a more preferred embodiment, the sodium salt is a trisodium citrate. In an even more preferred embodiment, the citrate salt is a sodium citrate dihydrate or a trisodium citrate dihydrate.

In a more preferred embodiment, the one or more buffers is present in compositions of the present invention at a concentration from about 0.01% to about 2.0% w/v, more preferably from about 0.1% to about 1.5% w/v and most preferably at about 0.22% w/v or about 1.02% w/v.

In another more preferred embodiment, citric acid is present in compositions of the present invention at a concentration from about 0.01% to about 1.0% w/v, more preferably from about 0.1% to about 0.3% w/v or from about 0.15% to about 0.45% w/v and most preferably at about 0.16% w/v or about 0.28% w/v.

In another more preferred embodiment, the citrate salt is present in compositions of the present invention at a concentration from about 0.01% to about 2.0% w/v, more preferably from about 0.02% to about 0.08% w/v or from about 0.5% to about 1.0% w/v and most preferably at about 0.06% w/v or about 0.74% w/v.

In a preferred embodiment liquid pharmaceutical compositions of the present invention may have a pH from about 2 to about 10, preferably from about 2 to about 7, more preferably from about 3 to about 6 and most preferably at about 3.55, about 5.0 or about 5.6.

In another embodiment, liquid pharmaceutical compositions of the present invention may contain an antimicrobial agent. Antimicrobial agents suitable for use in the present invention include, but are not limited to, benzyl alcohol, benzalkonium chloride, parabens including methylparaben, propylparaben, chlorobutanol, edetate, citrate, pentetate, tromethamine, sorbate, ascorbate, sodium benzoate, sulfites containing agents and mixtures thereof. In a preferred embodiment, the antimicrobial agent is selected from the group consisting of methylparaben, propylparaben, sodium benzoate and a combination thereof.

In a more preferred embodiment, the antimicrobial agent is present in compositions of the present invention at a concentration from about 0.01% to about 1.0% w/v, more preferably from about 0.05% to about 0.5% w/v and most preferably at about 0.1% w/v.

In another preferred embodiment, the liquid pharmaceutical compositions of present invention do not contain an antioxidant.

In another preferred embodiment, the liquid pharmaceutical compositions of present invention may contain an antioxidant. Antioxidants suitable for use in the present invention include, but are not limited to, butylated hydroxyanisole ("BHA"), butylated hydroxytoluene (BHT), methionine, sodium ascorbate, sodium thiosulfate, thioglycerol, ascorbic acid, ascorbyl palmitate, propyl gallate, dL-alpha-tocopherol, sodium sulfite, sodium metabisulfite, sodium bisulfite cysteine hydrochloride, glutathione and a mixture thereof. In a preferred embodiment, the antioxidant is BHA.

In a more preferred embodiment, when antioxidants are present in compositions of the present invention the antioxidants are present at a concentration from about from about 0.001% to about 1.0% w/v, preferably from about 0.005% to about 0.1% w/v and most preferably at about 0.01% w/v.

In another preferred embodiment, liquid pharmaceutical compositions of the present invention may contain a flavoring agent. Flavoring agents suitable for the present invention include, but are not limited to, peppermint oil, menthol, spearmint oil, citrus oil, cinnamon oil, strawberry flavor, cherry flavor, raspberry flavor, orange oil and a combination thereof. In a preferred embodiment, the flavoring agent is strawberry flavor.

In a more preferred embodiment, the flavoring agent is present in compositions of the present invention at a concentration from about 0.001% to about 0.1% w/v, more preferably from about 0.005% to about 0.05% w/v and most preferably at about 0.01% w/v.

In another preferred embodiment, liquid pharmaceutical compositions of the present invention may contain a sweetener. Sweeteners suitable for use in the present invention include, but are not limited to, sucralose, sucrose, aspartame, saccharin, dextrose, mannitol, glycerin, xylitol and combinations thereof. In a preferred embodiment, the sweetener is sucralose.

In a more preferred embodiment, the sweetener is present in compositions of the present invention at a concentration from about 0.0001% to about 0.01% w/v, more preferably from about 0.001% to about 0.005% w/v and most preferably at about 0.003% w/v.

In another preferred embodiment, the present invention is directed to liquid pharmaceutical compositions comprising from about 0.001% to about 0.1% w/v rasagiline or a pharmaceutically acceptable salt thereof and a liquid vehicle comprising from about 10% to about 90% w/v water and from about 10% to about 90% w/v glycerin.

In another embodiment, the present invention is directed to a liquid pharmaceutical composition comprising about 0.03% w/v rasagiline mesylate, about 53% w/v water and about 60% w/v glycerin.

In a more preferred embodiment, the present invention is directed to a liquid pharmaceutical composition comprising about 0.031% w/v rasagiline mesylate, about 60% w/v glycerin, about 52.636% w/v water, about 0.10% w/v sodium benzoate, about 0.16% w/v citric acid, about 0.06% w/v of a citrate salt, about 0.010% w/v strawberry flavor and about 0.003% w/v sucralose.

In another embodiment, the present invention is directed to liquid pharmaceutical compositions comprising from about 0.001% to about 0.1% w/v ropinirole or a pharmaceutically acceptable salt thereof and a liquid vehicle comprising from about 10% to about 90% w/v water and from about 10% to about 90% w/v propylene glycol.

In another embodiment, the present invention is directed to a liquid pharmaceutical composition comprising about 0.02% w/v ropinirole hydrochloride, about 55% w/v water and about 46.3% w/v propylene glycol.

In a more preferred embodiment, the present invention is directed to a liquid pharmaceutical composition comprising about 0.02% w/v ropinirole hydrochloride, about 46.3% w/v propylene glycol, about 55.63% w/v water, about 0.28% w/v citric acid, about 0.74% w/v of a citrate salt and optionally, about 0.02% w/v butylated hydroxyanisole.

In another embodiment, the compositions of the present invention provide stability of the active ingredient. Preferably the active ingredients of the compositions of the present invention maintain at least 90% initial assay value for one week at 40° C., more preferably at least 90% initial assay value for two weeks at 40° C. and even more preferably at least 90% initial assay value for four weeks at 40° C. Further and preferably the compositions of the present invention contain less than 4% w/v total impurities following incubation for 144 hours at 60° C., more preferably less than 3% w/v total impurities following incubation for 144 hours at 60° C., even more preferably less than 2% w/v total impurities following incubation for 144 hours at 60° C. and most preferably less than 1% w/v total impurities following incubation for 144 hours at 60° C.

In another embodiment, the present invention is directed to methods of treating Parkinson's disease comprising administering an effective amount of a liquid pharmaceutical composition of the present invention to a subject in need thereof.

In another embodiment, the present invention is directed to methods of treating one or more symptoms of Parkinson's disease comprising administering an effective amount of a liquid pharmaceutical composition of the present invention to a subject in need thereof.

In a preferred embodiment, administration of the liquid pharmaceutical compositions of the present invention occur via the oral route.

In another preferred embodiment, administration of the liquid pharmaceutical compositions of the present invention occurs via a feeding tube.

In another embodiment, the present invention is directed to methods for detecting the presence of an active ingredient selected from the group consisting of rasagiline, ropinirole or a pharmaceutically acceptable salt thereof in a fluid sample comprising:
  a) providing a detecting agent;
  b) contacting the detecting agent with the fluid sample; and
  c) determining the presence of the active ingredient bound to the detecting agent.

In a preferred embodiment, the presence of the active ingredient bound to the detecting agent is determined by fluorescence.

In another embodiment, the present invention is directed to methods for determining purity of an active compound selected from the group consisting of rasagiline, ropinirole or a pharmaceutically acceptable salt thereof in a fluid sample comprising:
  a) dissolving the fluid sample in a first solvent to produce a sample solution;
  b) dissolving a pure sample of the active compound in a second solvent to produce a reference solution;
  c) subjecting the sample solution to a chromatic technique comprising a stationary phase;
  d) subjecting the reference solution to the chromatic technique; and
  e) comparing the results of c) and d) to determine the presence of one or more related substances in the sample solution.

In a preferred embodiment, the first solvent and the second solvent are each independently selected from the group consisting of an aqueous buffer, an organic solvent and a combination thereof.

In another preferred embodiment, the stationary phase is selected from the group consisting of a reverse phase (hydrophobic), octylsilyl silica gel, octadecylsilyl silica gel, phenyl gel and a combination thereof.

In another preferred embodiment, the liquid pharmaceutical compositions of the present invention containing rasagiline or a pharmaceutically acceptable salt thereof are administered at an amount of from about 0.1 to about 5.0 milligrams rasagiline, preferably from about 0.5 to about 1.0 milligrams.

In another preferred embodiment, the liquid pharmaceutical compositions of the present invention containing ropinirole or a pharmaceutically acceptable salt thereof are administered at an amount of from about 0.1 to about 20.0 milligrams ropinirole, preferably from about 0.25 to about 12.0 milligrams.

As used herein the term "pharmaceutically acceptable" refers to ingredients that are not biologically or otherwise undesirable in an oral application.

As used herein, all numerical values relating to amounts, weights, and the like, are defined as "about" each particular value, that is, plus or minus 10%. For example, the phrase "10% w/w" is to be understood as "9% to 11% w/w." Therefore, amounts within 10% of the claimed value are encompassed by the scope of the claims.

As used herein "% w/w" refers to the weight percent by weight of the total formulation.

As used herein "% w/v" refers to the weight percent by volume of the total formulation.

As used herein the term "effective amount" refers to the amount necessary to treat a patient in need thereof.

As used herein the term "treatment" or "treating" refers to alleviating or ameliorating Parkinson's disease or symptoms of Parkinson's disease.

As used herein, the term "stable" includes, but is not limited to, physical and chemical stability.

Pharmaceutically acceptable salts of that can be used in accordance with the current invention include but are not limited to hydrochloride, dihydrate hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, mesylate, maleate, gentisinate, fumarate, tannate, sulphate, tosylate, esylate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts.

Throughout the application, the singular forms "a," "an," and "the" include plural reference unless the context clearly dictates otherwise.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to use the formulations of the invention. They are not intended to be limiting in any way.

EXAMPLES

Example 1—Rasagiline Vehicle Stability Screening

Method

Rasagiline mesylate was added separately to various combinations of water, propylene glycol, sorbitol and glycerin at a 0.04% w/w concentration. Each formulation was then placed at 60° C. for 168 hours. Rasagiline mesylate assay and degradants were recorded at time 0 and 168 hours. Results of this study are shown in Table 1, below.

Results

As seen in Table 1, below, Formulation C resulted in an increase in rasagiline mesylate assay. This result is likely due to homogeneity problems and thus sorbitol was determined to not be a candidate vehicle. The high assay value of Formulation D was determined to be due to either lack of homogeneity or operator error. Formulation E was determined to suffer from homogeneity issues due to the sharp decrease in assay without increase in degradants. Based on these results it was determined that water is an essential component of rasagiline mesylate liquid formulations.

TABLE 1

| Rasagiline in Various Vehicles | | | | | |
|---|---|---|---|---|---|
| (% w/w) | A | B | C | D | E |
| Rasagiline Mesylate | 0.04 | 0.04 | 0.04 | 0.04 | 0.04 |
| Water | 99.96 | 49.98 | 28.56 | 49.98 | — |
| Propylene Glycol | — | 49.98 | — | — | 49.98 |
| Sorbitol | — | — | 71.40 | — | — |
| Glycerin | — | — | — | 49.98 | 49.98 |
| Assay t = 0 | 95 | 100 | 95 | 145 | 112 |
| Assay t = 168 hours at 60° C. | 94 | 99 | 104 | 144 | 60 |
| Degradants t = 0 | ND | ND | ND | ND | ND |
| Degradants t = 168 hours at 60° C. | 0.1 | ND | ND | ND | ND |

ND = not detected

Example 2—Rasagiline pH Stability Screening

Method

To determine pH stability of liquid rasagiline mesylate formulations the four formulations of Table 2, below, were prepared as follows: 1) propylene glycol was added to a $1^{st}$ beaker and stirring was begun; 2) parabens were added to the $1^{st}$ beaker and mixed until dissolved, 3) water was added to a $2^{nd}$ beaker and stirring was begun; 4) glycerin was added to the $2^{nd}$ beaker and mixed until uniformity was obtained; 5) rasagiline mesylate was added to the $2^{nd}$ beaker and mixed until dissolved; 6) contents of $1^{st}$ beaker was added to $2^{nd}$ beaker and mixed until uniformity was obtained; 7) all other components were added while stirring, 8) buffer ratios adjusted until target pH was obtained while stirring; and 9) water was added to final volume. Each formulation was then placed at 60° C. for 26 days and also at 40° C. and 75% relative humidity ("RH") for 1 month. Rasagiline mesylate assay, methylparaben assay and propylparaben assay and degradants were recorded at time 0, 26 days and 1 month. Results of this study are shown in Table 3, below.

Results

As seen in Table 3, below, all formulations maintained comparable assay results and degradant amounts. Thus, liquid rasagiline formulations are stable across a range of pH's.

TABLE 2

| Rasagiline pH Stability Formulations | | | | |
|---|---|---|---|---|
| (% w/v) | F | G | H | I |
| Rasagiline Mesylate | 0.031 | 0.031 | 0.031 | 0.031 |
| Glycerin | 50 | 50 | 50 | 50 |
| Propylene Glycol | 10 | 10 | 10 | 10 |
| Methylparaben | 0.22 | 0.22 | 0.22 | 0.22 |
| Propylparaben | 0.05 | 0.05 | 0.05 | 0.05 |
| Purified Water | 50.559 | 51.325 | 51.075 | 51.699 |
| Citric Acid | 0.06 | 0.24 | 0.069 | — |
| Trisodium Citrate Dihydrate | 0.080 | 0.134 | 0.555 | — |
| Target pH | 5 | 4 | 6 | none |
| Actual pH | 4.96 | 3.95 | 6.26 | 6.21 |
| Density* | 1.11 | 1.12 | 1.12 | 1.12 |

*Due to density being greater than 1 the total % w/v is greater than 100%.

TABLE 3

Rasagiline pH Stability

| Formulation | F | G | H | I |
|---|---|---|---|---|
| Rasagiline Assay | | | | |
| t = 0 | 96.1 | 96.6 | 98.0 | 97.0 |
| t = 26 days at 60° C. | 97.1 | 99.0 | 94.0 | 98.0 |
| t = 1 month at 40° C. | 95.8 | 96.6 | 96.6 | 96.3 |
| Methylparaben Assay | | | | |
| t = 0 | 96.2 | 97.3 | 98.4 | 98.5 |
| t = 26 days at 60° C. | 95.5 | 98.7 | 82.6 | 96.4 |
| t = 1 month at 40° C. | 95.0 | 97.0 | 95.3 | 97.2 |
| Propylparaben Assay | | | | |
| t = 0 | 90.3 | 92.0 | 92.8 | 91.3 |
| t = 26 days at 60° C. | 94.8 | 98.7 | 95.3 | 97.7 |
| t = 1 month at 40° C. | 91.8 | 96.2 | 93.0 | 95.8 |
| Total Degradants | | | | |
| t = 0 | 0.1 | ND | 0.7 | 0.1 |
| t = 26 days at 60° C. | 0.3 | 0.1 | 1.12 | 0.1 |
| t = 1 month at 40° C. | ND | ND | 0.2 | ND |

Example 3—Rasagiline Water Concentration Stability Screening

Method

To determine the effect of water concentration on liquid rasagiline mesylate formulations the two formulations of Table 4, below, were prepared as in Example 2, above. Each formulation was then placed at 60° C. for 26 days and also at 40° C. 75% RH for 3 months. Rasagiline mesylate assay, methylparaben assay and propylparaben assay and degradants were recorded at time 0, 26 days and 1 month. Results of this study are shown in Table 5, below.

Results

As seen in Table 5, below, both 9% and 59% water formulations maintained comparable assay results and degradant amounts. Thus, liquid rasagiline formulations are stable across a range of water concentrations.

TABLE 4

Rasagiline pH Stability Formulations

| (% w/v) | J | K |
|---|---|---|
| Rasagiline Mesylate | 0.031 | 0.031 |
| Glycerin | 25 | 75 |
| Propylene Glycol | 10 | 10 |
| Methylparaben | 0.22 | 0.22 |
| Propylparaben | 0.05 | 0.05 |
| Purified Water | 66.399 | 23.399 |
| Citric Acid | 0.1 | 0.1 |
| Trisodium Citrate Dihydrate | 0.2 | 0.2 |
| Target pH | 5 | 5 |
| Actual pH | 5.01 | 5.05 |
| Density* | 1.07 | 1.14 |

*Due to density being greater than 1 the total % w/v is greater than 100%.

TABLE 5

Rasagiline pH Stability

| Formulation | J | K |
|---|---|---|
| Rasagiline Assay | | |
| t = 0 | 98.1 | 97.8 |
| t = 26 days at 60° C. | 99.1 | 97.2 |
| t = 1 month at 40° C. | 96.9 | 89.9 |
| Methylparaben Assay | | |
| t = 0 | 98.4 | 95.5 |
| t = 26 days at 60° C. | 97.6 | 96.4 |
| t = 1 month at 40° C. | 97.2 | 97.9 |
| Propylparaben Assay | | |
| t = 0 | 94.9 | 97.7 |
| t = 26 days at 60° C. | 98.3 | 97.2 |
| t = 1 month at 40° C. | 96.5 | 96.1 |
| Total Degradants | | |
| t = 0 | 0.1 | ND |
| t = 26 days at 60° C. | ND | 0.6 |
| t = 1 month at 40° C. | ND | ND |
| t = 3 month at 40° C. | 0.3 | — |

Example 4—Rasagiline Antimicrobial Preservative Type Screening

Method

To determine the effect of preservative type on liquid rasagiline mesylate Formulation L of Table 6, below, was prepared as follow: 1) water was added to a beaker and stirring was begun; 2) glycerin was added to the beaker and mixed until uniformity was obtained; 3) rasagiline was added to the beaker and mixed until dissolved; 4) sodium benzoate was added and mixed until dissolved; 5) all other ingredients were added and mixed until dissolved; 6) buffer ratios adjusted until target pH was obtained while stirring and 7) water was added to final volume. Formulation L was then placed at 60° C. for 26 days and also at 40° C. 75% RH for 3 months. Rasagiline mesylate assay and degradants were recorded at time 0, 26 days, 1 month and 3 months for Formulation L and compared to Formulation G, from Table 2, above. Results of this study are shown in Table 7, below.

Results

As seen in Table 7, below, sodium benzoate maintained a superior rasagiline mesylate assay as compared to a combination of methyl- and propylparaben. Thus, liquid rasagiline formulations may benefit from the addition of sodium benzoate.

TABLE 6

Rasagiline Antimicrobial Type Formulations

| (% w/v) | G | L |
|---|---|---|
| Rasagiline Mesylate | 0.031 | 0.031 |
| Glycerin | 50 | 60 |
| Propylene Glycol | 10 | — |
| Methylparaben | 0.22 | — |
| Propylparaben | 0.05 | — |
| Sodium Benzoate | — | 0.1 |
| Purified Water | 51.325 | 53.226 |
| Citric Acid | 0.24 | 0.576 |
| Trisodium Citrate Dihydrate | 0.134 | 0.067 |
| Target pH | 4 | 3 |
| Actual pH | 3.95 | 3.09 |
| Density* | 1.12 | 1.14 |

*Due to density being greater than 1 the total % w/v is greater than 100%.

TABLE 7

| Rasagiline Antimicrobial Type Stability | | |
|---|---|---|
| Formulation | G | L |
| Rasagiline Assay | | |
| t = 0 | 96.6 | 99.2 |
| t = 26 days at 60° C. | 99.0 | 100 |
| t = 1 month at 40° C. | 96.6 | 99.3 |
| Total Degradants | | |
| t = 0 | ND | ND |
| t = 26 days at 60° C. | 0.1 | ND |
| t = 1 month at 40° C. | ND | ND |
| t = 3 month at 40° C. | — | ND |

Example 5—Rasagiline Antioxidant Preservative Type Screening

Method

To determine the effect of preservative type on liquid rasagiline mesylate Formulation M of Table 8, below, was prepared as in Example 2, above. Formulation M was then placed at 60° C. for 26 days and also at 40° C. 75% RH for 1 month. Rasagiline mesylate assay and degradants were recorded at time 0, 26 days and 1 month for Formulation M and compared to Formulation F, from Table 2, above. Results of this study are shown in Table 9, below.

Results

As seen in Table 8, below, the addition of an antioxidant maintained a superior rasagiline mesylate assay as compared to a formulation without an antioxidant. Thus, liquid rasagiline formulations may benefit from the addition of an antioxidant.

TABLE 7

| Rasagiline Antioxidant Type Formulations | | |
|---|---|---|
| (% w/v) | F | M |
| Rasagiline Mesylate | 0.031 | 0.031 |
| Glycerin | 50 | 50 |
| Propylene Glycol | 10 | 10 |
| Methylparaben | 0.22 | 0.22 |
| Propylparaben | 0.05 | 0.05 |
| Butylated Hydroxyanisole | — | 0.01 |
| Purified Water | 50.559 | 50.488 |
| Citric Acid | 0.06 | 0.067 |
| Trisodium Citrate Dihydrate | 0.080 | 0.134 |
| Target pH | 5 | 5 |
| Actual pH | 4.96 | 4.96 |
| Density* | 1.11 | 1.11 |

*Due to density being greater than 1 the total % w/v is greater than 100%.

TABLE 8

| Rasagiline Antimicrobial Type Stability | | |
|---|---|---|
| Formulation | F | M |
| Rasagiline Assay | | |
| t = 0 | 96.1 | 99.9 |
| t = 26 days at 60° C. | 97.1 | 99.2 |
| t = 1 month at 40° C. | 95.8 | 98.7 |
| Methylparaben Assay | | |
| t = 0 | 96.2 | 97.4 |
| t = 26 days at 60° C. | 95.5 | 96.1 |
| t = 1 month at 40° C. | 95.0 | 96.8 |
| Propylparaben Assay | | |
| t = 0 | 90.3 | 91.1 |
| t = 26 days at 60° C. | 94.8 | 97.1 |
| t = 1 month at 40° C. | 91.8 | 92.0 |
| Total Degradants | | |
| t = 0 | 0.1 | ND |
| t = 26 days at 60° C. | 0.3 | 0.51 |
| t = 1 month at 40° C. | ND | ND |

Example 6—Rasagiline Antimicrobial Preservative Concentration Screening

Method

To determine the effect of preservative concentration on liquid rasagiline mesylate formulations of Table 9, below, were prepared as in Example 4, above. Separate vials containing each formulation were then each inoculated with *Staphylococcus aureus, Pseudomonas aeruginosa, Escherichia coli, Candida albicans* or *Aspergillus brasiliensis* and incubated for 28 days. Colony forming units were counted on day 14 and day 28. Results of this study are shown in Table 10, below as a log reduction from day 1 colony forming unit counts.

Results

As seen in Table 10, below, the addition of 0.1% w/v sodium benzoate provided superior antimicrobial properties to 0.05% w/v or no sodium benzoate. Thus, liquid rasagiline formulations may benefit from the addition of 0.1% w/v sodium benzoate.

TABLE 9

| Rasagiline Antimicrobial Concentration Formulations | | | |
|---|---|---|---|
| (% w/v) | N | O | P |
| Rasagiline Mesylate | 0.031 | 0.031 | 0.031 |
| Glycerin | 60 | 60 | 60 |
| Sodium Benzoate | — | 0.05 | 0.10 |
| Purified Water | 51.744 | 51.694 | 52.644 |
| Citric Acid | 0.156 | 0.156 | 0.156 |
| Trisodium Citrate Dihydrate | 0.056 | 0.056 | 0.056 |
| Strawberry Flavor | 0.01 | 0.01 | 0.01 |
| Sucralose | 0.003 | 0.003 | 0.003 |
| Density* | 1.12 | 1.12 | 1.13 |

*Due to density being greater than 1 the total % w/v is greater than 100%.

TABLE 10

| Rasagiline Antimicrobial Concentration Efficacy | | | | | | |
|---|---|---|---|---|---|---|
| Log Reduction from Initial | Formulation N | | Formulation O | | Formulation P | |
| CFU/mL | 14 day | 28 day | 14 day | 28 day | 14 day | 28 day |
| *C. albicans* | 3.5 | >4.0 | 1.1 | >4.0 | 2.3 | >4.0 |
| *E. coli* | >4.2 | 0.0 | >4.2 | 0.0 | >4.2 | 0.0 |
| *P. aeruginosa* | >4.5 | 0.0 | >4.5 | 0.0 | >4.5 | 0.0 |
| *S. aureus* | >4.0 | 0.0 | >4.0 | 0.0 | >4.0 | 0.0 |
| *A. brasiliensis* | 0.3 | −0.2 | 1.2 | 1.1 | >3.6 | >3.6 |

Example 7—Ropinirole Vehicle Stability Screening

Method

Ropinirole hydrochloride was added separately to various combinations of water, propylene glycol, sorbitol and glycerin at a 0.02% w/v concentration. Each formulation was then placed at 60° C. for 144 hours. Impurities were recorded at time 0 and 144 hours. Results of this study are shown in Table 11, below.

Results

As seen in Table 11, below, significant degradation of ropinirole hydrochloride occurred in all the formulations. However, degradation was minimized in the propylene glycol and glycerin formulations. Thus, ropinirole hydrochloride degradation can be minimized by using more hydrophobic solvents.

TABLE 11

Ropinirole in Various Vehicles

| (% w/v) | 1 | 2 | 3 | 4 | 5 |
|---|---|---|---|---|---|
| Ropinirole Hydrochloride | 0.02 | 0.02 | 0.02 | 0.02 | 0.02 |
| Water | 98.98 | — | — | — | 50 |
| Glycerin | — | 124.98 | — | — | 66.98 |
| Propylene Glycol | — | — | 103.98 | — | — |
| Sorbitol | — | — | — | 130.98 | — |
| Target pH | 5.0 | 5.0 | 5.0 | 5.0 | 5.0 |
| Density* | 0.99 | 1.25 | 1.04 | 1.31 | 1.17 |
| Total Impurities time 0 | 0.71 | 0.22 | 0.31 | 0.57 | 0.22 |
| Total Impurities 144 hours | 3.50 | 2.04 | 0.74 | 1.01 | 3.10 |

*Due to density being greater than 1 the total % w/v is greater than 100%.

Example 8—Ropinirole Antioxidant Preservative Type Screening

Method

To determine the effect of preservative type liquid ropinirole formulations of Table 12, below, were placed at 60° C. for 144 hours. Impurities were recorded at time 0 and 144 hours. Results of this study are shown in Table 12, below.

Results

As seen in Table 12, below, the citrate buffer system of citric acid and trisodium citrate dihydrate sufficiently prevented the formation of impurities. This antioxidant effect was not negatively impacted by the addition of butylated hydroxyanisole. However, EDTA and ascorbic acid did not sufficiently inhibit the formulation of impurities in the absence of the citrate buffer system. Thus, liquid ropinirole formulations containing a citrate buffer system may benefit from the addition of an antioxidant.

TABLE 12

Ropinirole Antioxidant Type Formulations

| (% w/v) | 6 | 7 | 8 | 9 | 10 | 11 |
|---|---|---|---|---|---|---|
| Ropinirole Hydrochloride | 0.02 | 0.02 | 0.02 | 0.02 | 0.02 | 0.02 |
| Water | 54.64 | 54.66 | 55.63 | 55.63 | 54.46 | 55.16 |
| Propylene Glycol | 46.3 | 46.3 | 46.3 | 46.3 | 46.3 | 46.3 |
| Citric Acid | 0.28 | 0.28 | — | — | 0.28 | 0.28 |
| Trisodium Citrate Dihydrate | 0.74 | 0.74 | — | — | — | — |
| Sodium Citrate Dihydrate | — | — | — | — | 0.74 | 0.74 |
| Butylated Hydroxyanisole | 0.02 | — | — | — | — | — |
| EDTA | — | — | 0.05 | — | — | — |
| Ascorbic Acid | — | — | — | 0.05 | — | — |
| Methylparaben | — | — | — | — | 0.18 | — |
| Propylparaben | — | — | — | — | 0.02 | — |
| Sodium Benzoate | — | — | — | — | — | 0.5 |
| Target pH | 5.0 | 5.0 | 5.0 | 5.0 | 5.0 | 5.0 |
| Density* | 1.02 | 1.02 | 1.02 | 1.02 | 1.02 | 1.03 |
| Total Impurities time 0 | 0.00 | 0.00 | 3.06 | 0.57 | — | — |
| Total Impurities 144 hours | 0.00 | 0.00 | 3.33 | 0.82 | — | — |

*Due to density being greater than 1 the total % w/v is greater than 100%.

What is claimed is:

1. A liquid pharmaceutical composition comprising about 0.03% w/v rasagiline mesylate, about 53% w/v water, about 60% w/v glycerin, from about 0.06% to about 0.16% w/v citric acid, from about 0.06% to about 0.5% w/v of a citrate salt, about 0.18% w/v methylparaben and about 0.02% w/v propylparaben, wherein w/v denotes weight by total volume of the composition.

2. A method of treating Parkinson's disease comprising administering an effective amount of the composition of claim 1 to a subject in need thereof.

3. A method of treating one or more symptoms of Parkinson's disease comprising administering an effective amount of the composition of claim 1 to a subject in need thereof.

* * * * *